(12) United States Patent
Hyde

(10) Patent No.: US 12,127,939 B2
(45) Date of Patent: Oct. 29, 2024

(54) CATHETER LUMEN LUBRICANT

(71) Applicant: Cephea Valve Technologies, Inc., Santa Clara, CA (US)

(72) Inventor: Gregory M. Hyde, Menlo Park, CA (US)

(73) Assignee: Cephea Valve Technologies, Inc., Abbott Park, IL (US)

( * ) Notice: Subject to any disclaimer, the term of this patent is extended or adjusted under 35 U.S.C. 154(b) by 734 days.

(21) Appl. No.: 17/215,101

(22) Filed: Mar. 29, 2021

(65) Prior Publication Data

US 2021/0338425 A1   Nov. 4, 2021

Related U.S. Application Data

(60) Provisional application No. 63/017,903, filed on Apr. 30, 2020.

(51) Int. Cl.
*A61F 2/24* (2006.01)
*A61M 25/00* (2006.01)

(52) U.S. Cl.
CPC ....... *A61F 2/2436* (2013.01); *A61M 25/0043* (2013.01); *A61M 2025/0062* (2013.01)

(58) Field of Classification Search
None
See application file for complete search history.

(56) References Cited

U.S. PATENT DOCUMENTS

| 5,634,928 | A  | * | 6/1997  | Fischell | A61F 2/95 |
|           |    |   |         |          | 623/1.11  |
| 6,221,097 | B1 |   | 4/2001  | Wang     |           |
| 6,331,186 | B1 | * | 12/2001 | Wang     | A61F 2/958 |
|           |    |   |         |          | 623/1.11  |
| 6,530,946 | B1 | * | 3/2003  | Noda     | A61F 7/123 |
|           |    |   |         |          | 607/113   |
| 6,530,947 | B1 |   | 3/2003  | Euteneuer |          |
| 6,859,986 | B2 |   | 3/2005  | Jackson  |           |
| 7,309,349 | B2 |   | 12/2007 | Jackson  |           |
| 8,858,608 | B2 |   | 10/2014 | Grewe    |           |
| 10,568,753 | B2 |  | 2/2020  | Epstein  |           |
| 2001/0034548 | A1 | * | 10/2001 | Vrba  | A61F 2/966 |
|           |    |   |         |          | 623/1.11  |
| 2002/0022849 | A1 | * | 2/2002 | Sydney | A61F 2/958 |
|           |    |   |         |          | 604/103.08 |

(Continued)

*Primary Examiner* — Shaun L David

(74) *Attorney, Agent, or Firm* — SLEMAN & LUND LLP

(57) ABSTRACT

A catheter assembly for delivering a medical implant may include an inner shaft around which a compartment is defined, the compartment being adapted to receive the medical implant therein. The catheter assembly may include an outer shaft coaxially surrounding at least a portion of the inner shaft and movable in longitudinal directions relative to the inner shaft. The outer shaft may define a lumen therein, the inner shaft and the outer shaft together defining a space therebetween, the space providing liquid communication between a proximal end of the catheter assembly and the compartment. The catheter assembly may include a distal sheath fixedly connected to the outer shaft, the distal sheath being movable between a closed condition covering the compartment and an open condition uncovering the compartment for deployment of the medical implant. A lubricant containing albumin may be disposed within at least a portion of the space.

7 Claims, 1 Drawing Sheet

(56) References Cited

U.S. PATENT DOCUMENTS

| | | | |
|---|---|---|---|
| 2003/0004537 A1* | 1/2003 | Boyle | 606/200 |
| 2003/0163193 A1* | 8/2003 | Widenhouse | A61F 2/95 623/1.12 |
| 2003/0176910 A1* | 9/2003 | Vrba | A61F 2/95 623/1.11 |
| 2003/0233115 A1* | 12/2003 | Eversull | A61M 25/1002 606/194 |
| 2004/0148007 A1* | 7/2004 | Jackson | A61F 2/95 623/1.12 |
| 2004/0167603 A1* | 8/2004 | Jackson | A61F 2/915 623/1.12 |
| 2004/0175558 A1* | 9/2004 | El-Nounou | A61M 25/104 428/313.5 |
| 2004/0193177 A1* | 9/2004 | Houghton | A61F 2/958 606/108 |
| 2005/0182475 A1* | 8/2005 | Jen | A61F 2/95 606/191 |
| 2007/0202485 A1* | 8/2007 | Nees | A01N 1/0226 435/284.1 |
| 2008/0188928 A1* | 8/2008 | Salahieh | A61M 25/0054 623/2.11 |
| 2009/0099532 A1 | 4/2009 | Cuevas | |
| 2009/0099636 A1* | 4/2009 | Chanduszko | A61F 2/95 623/1.11 |
| 2010/0094392 A1* | 4/2010 | Nguyen | A61M 25/0023 623/1.11 |
| 2011/0125158 A1* | 5/2011 | Diwan | A61F 2/4657 606/93 |
| 2011/0172644 A1 | 7/2011 | Zanoni | |
| 2011/0190864 A1 | 8/2011 | Mcclain | |
| 2012/0083877 A1* | 4/2012 | Nguyen | A61F 2/2418 623/2.11 |
| 2012/0101456 A1* | 4/2012 | Forsell | A61L 27/26 604/264 |
| 2012/0143054 A1 | 6/2012 | Eaton | |
| 2013/0123757 A1* | 5/2013 | Crisostomo | A61M 25/0074 606/1 |
| 2013/0261722 A1* | 10/2013 | Hossainy | A61M 25/10 623/1.11 |
| 2017/0042669 A1* | 2/2017 | Backus | A61F 2/2412 |
| 2017/0258584 A1* | 9/2017 | Chang | A61F 2/2436 |
| 2019/0254819 A1* | 8/2019 | Hoffer | A61F 2/95 |
| 2020/0107843 A1* | 4/2020 | Goertz | A61B 17/2202 |
| 2021/0023276 A1* | 1/2021 | Cruise | A61L 29/085 |
| 2021/0153998 A1* | 5/2021 | Frisby | A61F 2/9525 |

\* cited by examiner

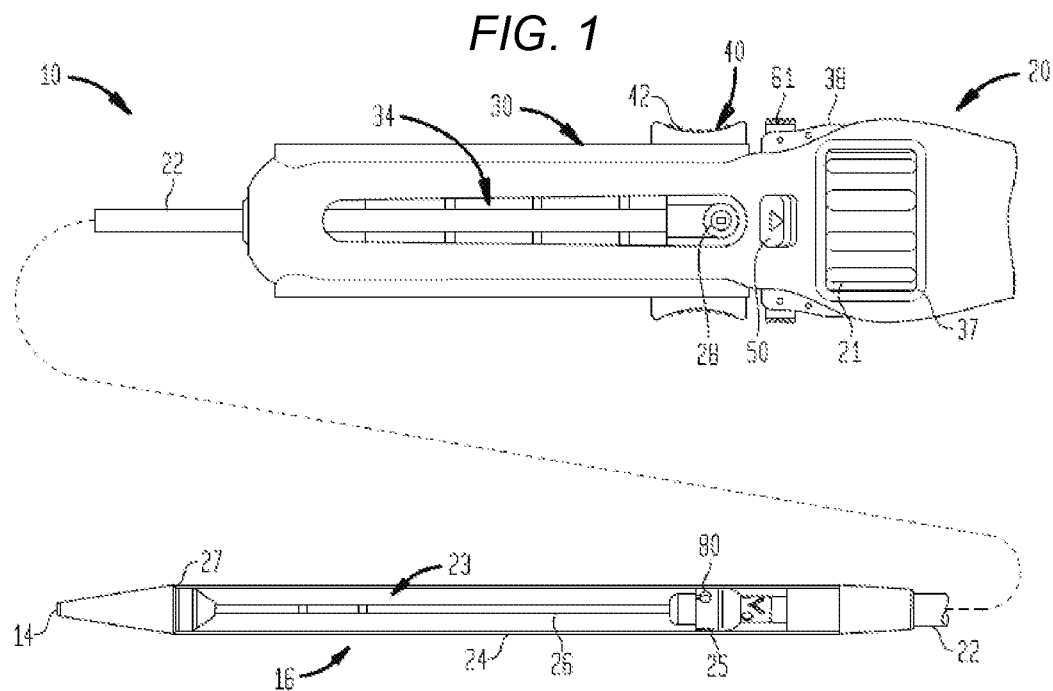
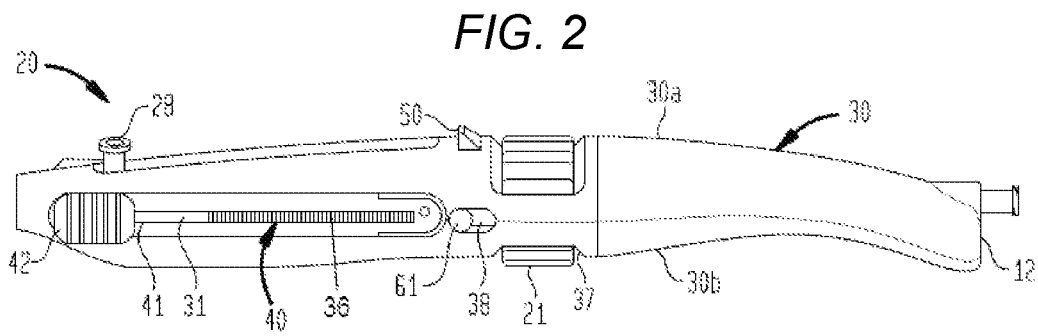
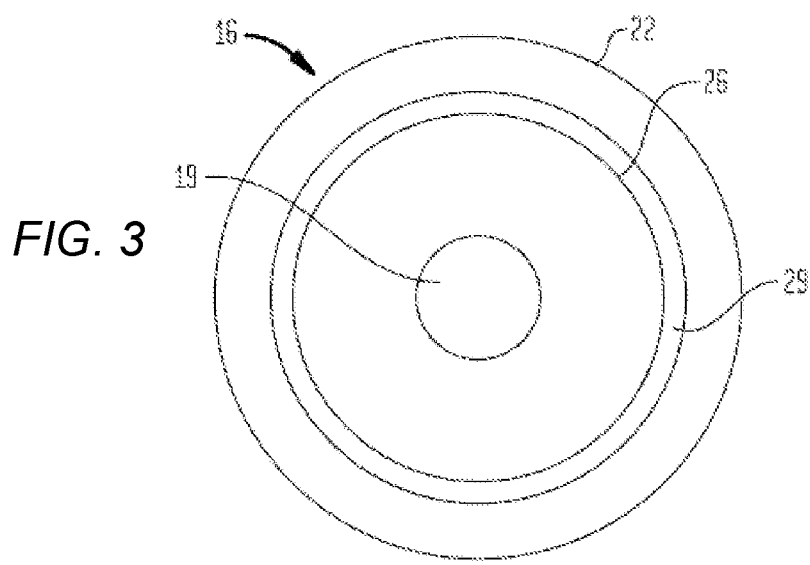

CATHETER LUMEN LUBRICANT

CROSS-REFERENCE TO RELATED APPLICATIONS

This application claims the benefit of the filing date of U.S. Provisional Patent Application No. 63/017,903 filed Apr. 30, 2020, the disclosure of which is hereby incorporated herein by reference

BACKGROUND OF THE INVENTION

The present invention is related to prosthetic heart valve replacement, and more particularly to devices, systems, and methods for transapical and transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from some shortcomings. For example, in conventional delivery devices for self-expanding valves, friction between the catheter assembly components can be excessive due to a tight clearance and/or twisting and binding between the inner and/or outer shafts of the delivery device.

BRIEF SUMMARY OF THE INVENTION

A catheter assembly for delivering a medical implant may include an inner shaft around which a compartment is defined, the compartment being adapted to receive the medical implant in an assembled condition, the inner shaft having a radially outward-facing surface. The catheter assembly may also include an outer shaft coaxially surrounding at least a portion of the inner shaft, the outer shaft being movable in longitudinal directions relative to the inner shaft, the outer shaft defining a lumen therein having a radially inward-facing surface, the inner shaft and the outer shaft together defining a space between the outward-facing surface of the inner shaft and the inward-facing surface of the outer shaft, the space providing liquid communication between a proximal end of the catheter assembly and the compartment. The catheter assembly may also include a distal sheath fixedly connected to the outer shaft, the distal sheath being movable in the longitudinal directions between a closed condition covering the compartment and an open condition uncovering the compartment for deployment of the medical implant. The catheter assembly may also include a lubricant containing albumin disposed within at least a portion of the space.

The inner shaft and the outer shaft each may include respective polymers. At least one of the inner shaft or the outer shaft may include a metal. The catheter assembly may be coupled to an operating handle, and the operating handle may include a hemostasis valve in liquid communication with the space. The catheter assembly may also include the medical implant disposed within the compartment. The medical implant may be a prosthetic heart valve. The catheter assembly may also include a recirculating pathway outside of the outer shaft providing liquid communication between the distal sheath and a proximal end of the catheter assembly.

A delivery device for a medical implant may include an operating handle having a housing, a carriage movable in longitudinal directions relative to the housing and a catheter assembly. The catheter assembly may include an inner shaft around which a compartment is defined, the inner shaft being operatively connected to the housing, the compartment being adapted to receive the medical implant in an assembled condition, the inner shaft having a radially outward-facing surface. The catheter assembly may also include an outer shaft coaxially surrounding at least a portion of the inner shaft, the outer shaft being fixedly connected to the carriage and movable in the longitudinal directions relative to the inner shaft and the housing, the outer shaft defining a lumen therein having a radially inward-facing surface, the inner shaft and the outer shaft together defining a space between the outward-facing surface of the inner shaft and the inward-facing surface of the outer shaft, the space providing liquid communication between the operating handle and the compartment. The catheter assembly may also include a distal sheath fixedly connected to the outer shaft, the distal sheath being movable in the longitudinal directions between a closed condition covering the compartment and an open condition uncovering the compartment for deployment of the medical implant. The catheter assembly may also include a lubricant containing albumin disposed within at least a portion of the space.

The inner shaft and the outer shaft each may include respective polymers. At least one of the inner shaft or the outer shaft may include a metal. The catheter assembly may be coupled to the operating handle, and the operating handle may include a hemostasis valve in liquid communication with the space. The catheter assembly may also include the medical implant disposed within the compartment. The medical implant may be a prosthetic heart valve. The catheter assembly may also include a recirculating pathway outside of the outer shaft providing liquid communication between the distal sheath and the operating handle.

A method of lubricating a catheter assembly that is configured to deliver a medical implant may include providing the catheter assembly, the catheter assembly including an inner shaft around which a compartment for the medical implant is defined, an outer shaft coaxially surrounding at least a portion of the inner shaft, and a distal sheath fixedly connected to the outer shaft, the distal sheath being movable in longitudinal directions between a fully closed condition covering the compartment and an open condition uncovering the compartment, the inner shaft and the outer shaft together defining a space therebetween providing liquid communication between a proximal end of the catheter assembly and the compartment. The method may also include mounting the medical implant in the compartment, sliding the distal sheath to cover the compartment and the medical implant, and flushing a lubricant containing albumin through the space either from the proximal end of the catheter assembly to the compartment or from the distal end of the compartment to the proximal end of the catheter assembly.

The catheter assembly may be coupled to an operating handle having a hemostasis valve in liquid communication with the space, and the flushing step may include flushing the lubricant through the hemostasis valve. The method may also include flowing the lubricant out of the compartment and recirculating the lubricant into the proximal end of the catheter assembly, or flowing the lubricant through the compartment and out the proximal end of the catheter assembly, and then recirculating the lubricant back into the compartment. The method may also include, before the mounting step, inserting the medical implant into a bath of the lubricant containing albumin. The method may also include inserting a distal end of the catheter assembly into a patient and deploying the medical implant by moving the distal sheath from the fully closed condition to the open condition. The method may further include flowing the lubricant through the compartment during the deploying step. The medical implant may be a prosthetic heart valve.

BRIEF DESCRIPTION OF THE DRAWINGS

Various embodiments of the present disclosure will now be described with reference to the appended drawings. It is to be appreciated that these drawings depict only some embodiments of the disclosure and are therefore not to be considered limiting of its scope.

FIG. 1 is a top plan view of a portion of an operating handle for a delivery device for transfemorally delivering a collapsible prosthetic heart valve, shown with a partial longitudinal cross-section of the distal portion of a transfemoral catheter assembly;

FIG. 2 is a side view of the handle of FIG. 1; and

FIG. 3 is a lateral cross-section through a catheter assembly suitable for use with the delivery device of FIG. 1.

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user. As used herein, the terms "generally," "substantially," "approximately," and "about" are intended to mean that slight deviations from absolute are included within the scope of the term so modified.

In the embodiments disclosed herein, a biocompatible, lubricious material may be used as a preparatory solution to lubricate the sliding elements of a catheter assembly of a delivery device, as will be described below. Such lubricious material may be plant-based and soluble in water. Another lubricious material that may be used in an aqueous solution is albumin, a normally occurring constituent of blood plasma. According to the present disclosure, a lubricant or a flushing liquid containing the lubricant may be applied to the catheter components in liquid form when assembled or may be applied during delivery device preparation, such as when albumin is used in a flushing liquid. In some examples, the lubricants disclosed herein (e.g., albumin) may also be used to lubricate a prosthetic valve or another medical implant being delivered by the delivery device, either before or after loading of the prosthetic valve into the catheter assembly. Such an albumin-based lubricant may provide advantages that a conventional flushing liquid, such as saline or heparinized saline, does not provide. In further examples, the lubricant may be incorporated in an aqueous solution, such as a heparinized saline solution, and administered at a slow flow rate from the delivery device as the delivery device is advanced to the target site and during deployment of the prosthetic valve.

Referring now to FIGS. 1-3, an exemplary delivery device 10 for transfemoral delivery of a collapsible prosthetic heart valve (or other types of collapsible stents) has a catheter assembly 16 for delivering the heart valve to and deploying the heart valve at a target location, and an operating handle 20 for controlling deployment of the valve from the catheter assembly. The delivery device 10 extends from a proximal end 12 (FIG. 2) to an atraumatic tip 14 at the distal end of catheter assembly 16. The catheter assembly 16 is adapted to receive a collapsible prosthetic heart valve (not shown) in a compartment 23 defined around an inner shaft 26 and covered by a distal sheath 24.

The inner shaft 26 may extend through the operating handle 20 to the atraumatic tip 14 of the delivery device, and includes a retainer 25 affixed thereto at a spaced distance from tip 14 and adapted to hold a collapsible prosthetic valve in the compartment 23. The inner shaft 26 may be made of a flexible material such as braided polyimide or polyetheretherketone (PEEK), for example. Using a material such as PEEK may improve the resistance of the inner shaft 26 to kinking while the catheter assembly 16 is tracking through the vasculature of a patient. The retainer 25 may have recesses 80 therein that are adapted to hold corresponding retention members of the prosthetic valve.

The distal sheath 24 surrounds the inner shaft 26 and is slidable relative to the inner shaft such that it can selectively cover or uncover the compartment 23. The distal sheath 24 is affixed at its proximal end to an outer shaft 22, the proximal end of which is connected to the operating handle 20. The distal end 27 of the distal sheath 24 abuts the atraumatic tip 14 when the distal sheath is fully covering the compartment 23, and is spaced apart from the atraumatic tip when the compartment 23 is at least partially uncovered. The inventive lubricant, which will be further described below, may be flushed into an annular space 29 extending between the outer shaft 22 and the inner shaft 26.

The operating handle 20 is adapted to control deployment of a prosthetic valve located in the compartment 23 by permitting a user to selectively slide the outer shaft 22 proximally or distally relative to the inner shaft 26, thereby respectively uncovering or covering the compartment with the distal sheath 24. The outer shaft 22 may be made of a flexible material such as nylon 11 or nylon 12, and it may have a round braid construction (i.e., round cross-section fibers braided together) or flat braid construction (i.e., rectangular cross-section fibers braided together), for example. The proximal end of the inner shaft 26 may be connected in substantially fixed relationship to an outer housing 30 of the operating handle 20, and the proximal end of the outer shaft 22 is affixed to a carriage assembly 40 that is slidable along a longitudinal axis of the handle housing, such that a user can selectively slide the outer shaft relative to the inner shaft by sliding the carriage assembly relative to the housing.

A hemostasis valve 28 includes an internal gasket adapted to create a seal between the inner shaft 26 and the proximal end of the outer shaft 22. The hemostasis valve 28 is in fluid communication with the compartment 23 via the space 29 (FIG. 3) between the inner shaft 26 and the outer shaft 22. At locations within the catheter assembly 16 between the operating handle 20 and the distal sheath 24, it is preferable that the inner diameter of the outer shaft 22 be slightly greater than the outer diameter of the inner shaft 26, so that the outer shaft can be slid in a longitudinal direction relative to the inner shaft without excessive friction between the shafts and without twisting and/or binding of the inner shaft within the outer shaft. For example, the inner diameter of the outer shaft 22 may be about 0.5 mm to about 1.0 mm greater than the outer diameter of the inner shaft 26, such that the space 29 has a lateral thickness of about 0.25 mm to about 0.5 mm.

The catheter assembly 16 is adapted to be flushed with a flushing liquid. It is desirable to flush the compartment 23 to de-air (i.e., remove air pockets or air bubbles) the area in and around the prosthetic valve, and/or to provide lubrication between an inward-facing surface of the outer shaft 22 and an outward-facing surface of the inner shaft 26. Such lubrication between the outer shaft 22 and the inner shaft 26 within the space 29 will reduce the friction between the two shafts during loading or deployment of the valve, and during resheathing of the valve if it is desired to reposition the valve during the deployment process. Reduced friction between the outer shaft 22 and the inner shaft 26 may permit more accurate unsheathing of the prosthetic valve, since excess friction can result in temporary binding of the outer and inner shafts that may result in sudden rapid movement of the distal sheath 24 during uncovering of the compartment 23.

To flush the space between the outer shaft 22 and the inner shaft 26, the user may apply a pressurized flushing liquid to the hemostasis valve 28. A proximal-to-distal pressure gradient in the lumen of the outer shaft 22 causes the flushing liquid to travel distally through the lumen. The flushing liquid may flow out of the lumen of the outer shaft 22, around the retainer 25, and into the compartment 23 within the distal sheath 24. The flushing liquid may flow out of the compartment 23 at the distal end 27 of the distal sheath 24 where the distal sheath abuts the atraumatic tip 14. A solution of lubricant may be flushed through the catheter as a one-time flush or recirculated constantly until the delivery device 10 is used in a patient. Such a constant recirculation may be achieved if the flushing liquid that flows out of the compartment 23 is recaptured and routed back into the hemostasis valve 28.

In an alternate arrangement, a distal flag valve may be applied to the distal end of the distal sheath 24, and a pressurized flushing liquid may be introduced through the flag valve into the compartment 23. A distal-to-proximal pressure gradient causes the flushing liquid to travel proximally through the compartment 23, around the retainer 25, into the lumen of the outer shaft 22 and then to the operating handle 20, where it exits the handle through one or more ports, including the hemostasis valve 28. A solution of lubricant may be flushed through the catheter as a one-time flush or may be recirculated constantly until the delivery device 10 is used in patient. Such a constant recirculation may be achieved if the flushing liquid that flows out of the ports in the operating handle 20 is recaptured and routed back into the distal flag valve and the compartment 23.

In a conventional delivery device, saline or heparinized saline is typically used to flush the valve compartment. A conventional hydrophilic lubricant coating may dry out and become sticky when used in a tight clearance location such as the space between the outer shaft 22 and the inner shaft 26. A conventional hydrophilic coating has to be cured, so it may not be able to properly coat a lumen of a shaft. Also, an annular space such as the space between the outer shaft 22 and the inner shaft 26 may be too small and get squeezed when the catheter assembly bends. Such catheter assembly bends may result in some lubricants becoming sticky and increasing friction between the sliding components. Moreover, a conventional hydrophilic lubricant coating may not be able to be placed on a metal shaft.

In a preferred embodiment, a particular blood constituent, albumin, may be used in a preparatory solution to lubricate the catheter sliding elements (the outer shaft 22 and the inner shaft 26). Since albumin absorbs water, it is lubricious, and it does not dry out when used in a tight space such as the space between the outer shaft 22 and the inner shaft 26. According to the present disclosure, a lubricant or a flushing liquid containing the lubricant may be applied to the catheter components in liquid form when assembled or may be applied during delivery device preparation, such as when albumin is used in a flushing liquid. In some examples, the lubricant may be a biological compound, an inorganic compound, a synthetic compound, or a natural oil. In some embodiments, cholesterol or a plant-based material, such as soybean oil, may also be used as the lubricant.

In some examples, a guidewire (not shown) may be used with the delivery device 10 during the delivery and deployment process. Such a guidewire may extend completely through the inner shaft 26 from the proximal end 12 of the delivery device 10 to the distal end of the atraumatic tip 14. A lubricant such as albumin may also or alternatively be used to flush the lumen of the inner shaft 26 in order to provide lubrication for a guide wire that may be inserted through the inner shaft for use during advancement of the delivery device 10 to the target location.

In particular examples, the lubricants disclosed herein (for example, albumin) may be used to lubricate a prosthetic valve being delivered by the delivery device 10, either before or after loading of the prosthetic valve into the compartment. For example, albumin may be used in a bath to keep a prosthetic valve hydrated before loading into a delivery device, and the albumin may remain on the valve to provide lubrication after loading into the delivery device. Alternatively, or in addition to using a bath, the catheter payload (e.g., a prosthetic valve) could be rinsed or coated with a lubricant such as albumin before loading into the delivery device. Such lubrication of the catheter payload before or after loading into the delivery device 10 may reduce the force required to retract the distal sheath 24 off of the implant, thereby reducing the force required for implant deployment.

The handle housing 30 includes a top portion 30a and a bottom portion 30b that collectively define an elongated space 34 in the housing 30 in which the carriage assembly 40 may travel. The elongated space 34 preferably permits the carriage assembly 40 to travel a distance that is at least as long as the anticipated length of the prosthetic valve to be delivered (e.g., at least about 50 mm), such that the distal sheath 24 can be fully retracted from around the prosthetic valve. A pair of slots 31 may be formed on opposite sides of the housing 30, contiguous with the elongated space 34. The length of the slots 31, minus the width of the carriage grip shafts (not shown), determines the maximum distance that the carriage assembly 40 can travel within the space 34.

The carriage assembly 40 has a body portion 41 with a threaded rod 36 extending proximally therefrom along the longitudinal axis of the housing 30. The handle housing 30 defines an enlarged bore that is sized to freely and slidingly receive the threaded rod 36. The enlarged bore has an inner diameter slightly larger than the outer diameter of the threaded rod 36. The threaded rod 36 preferably is longer than the anticipated maximum travel distance of the carriage assembly 40 within the elongated space 34 (e.g., at least about 50 mm), such that the threaded rod 36 does not fully disengage from the deployment actuator 21 (described below) during sheathing or resheathing of the prosthetic valve. The carriage assembly 40 further includes a pair of carriage grips 42 each attached to the body portion 41 by a respective carriage grip shaft. The carriage assembly 40 may include a resheathing lock adapted to limit the longitudinal movement of the carriage assembly proximally within the handle housing 30, thereby preventing the user from completing the deployment of a prosthetic valve when unintended. The resheathing lock may include a control member 50 that is pivotable relative to the housing 30 between a lock position and a release position.

The handle housing 30 further defines a pocket 37 that extends through the top portion 30a and bottom portion 30b for receiving deployment actuator 21. Deployment actuator 21 is internally threaded for selective engagement with the threaded rod 36. The pocket 37 is sized and shaped to receive the deployment actuator 21 with minimal clearance, such that the location of the deployment actuator remains substantially fixed relative to the housing 30 as it is rotated about the threaded rod 36. That is, when the deployment actuator 21 is in threaded engagement with the threaded rod 36, rotation of the deployment actuator in one direction (either clockwise or counterclockwise depending on the orientation of the threads on the threaded rod) causes the threaded rod to move proximally within the bore, at the same time pulling the body portion 41 of the carriage assembly 40 proximally through the elongated space 34. Similarly, when the deployment actuator 21 is in threaded engagement with the threaded rod 36, rotation of the deployment actuator in the opposite direction causes the threaded rod to move distally within the bore, at the same time pushing the body portion 41 of the carriage assembly 40 distally through the elongated space 34.

The deployment actuator 21 may be selectively placed in threaded engagement with the threaded rod 36 by a coupling assembly 61, which may be slidably received in longitudinal openings 38 formed on opposite lateral sides of the housing 30. The ability of the coupling assembly 61 to translate rotation of the deployment actuator 21 into translation of the carriage assembly 40 relative to the housing 30 may provide the user with the ability to carefully control movement of the carriage assembly both proximally within the space 34 during a valve deployment operation, and distally within the space 34 during a resheathing operation. The ability of the coupling assembly 61 to decouple the deployment actuator 21 from the carriage assembly 40 so that the carriage assembly can freely move longitudinally relative to the housing 30 enables gross movement of the carriage assembly proximally or distally within the space 34 without the mechanical advantage provided by the deployment actuator.

To use the operating handle 20 to deploy a prosthetic valve that has been loaded into the compartment 23 and covered by the distal sheath 24, the user may rotate the deployment actuator 21, causing the carriage assembly 40 to slide proximally within the elongated space 34 in the housing 30. Because the distal sheath 24 is affixed to the outer shaft 22, which in turn is affixed to the carriage assembly 40, and because the inner shaft 26 is fixed to the housing 30, sliding the carriage assembly proximally relative to the housing will retract the distal sheath proximally from the compartment 23, thereby exposing and initiating deployment of the valve located therein.

During valve deployment, the user can evaluate the position of the valve relative to the patient's aortic or mitral annulus and may be able to determine whether the valve is functioning properly. If repositioning or removal is desired, the user may resheathe the valve by rotating the deployment actuator 21 in the direction opposite that used for deployment. Such rotation will cause the threaded rod 36 to progress distally through the deployment actuator 21 until the carriage assembly 40 has reached the starting position shown in FIG. 2, thereby recollapsing the expanded part of the valve as the distal sheath 24 is moved distally over the compartment 23 and the partially deployed valve. With the valve resheathed, the user can reposition the delivery device 10 and can commence the deployment procedure once again or can simply remove the valve from the patient. When the valve has been completely unsheathed, the stent portion of the valve self-expands and disengages from the retainer 25, thereby releasing the valve from the catheter assembly 16.

In a further embodiment, an aqueous solution including a lubricant may be dispensed from the delivery device at a slow flow rate as the delivery device is advanced to the target site and during deployment of the prosthetic valve. In one example, a heparinized saline solution containing albumin (or another lubricant) could be used as a lubricious flushing liquid to flush the catheter assembly 16 prior to advancing the catheter assembly into the patient. The flushing liquid should have a sufficient amount of lubricant to provide a beneficial increase in lubrication over the flushing liquid without the lubricant, but not so much as to be clinically unsafe or to create too much viscosity such that there is increased friction in the operation of the catheter assembly. A check valve can be used to maintain a predetermined pressure of the lubricious flushing liquid within the catheter assembly as the catheter assembly is advanced to the target site. Once deployment of the prosthetic valve is commenced by retracting the distal sheath 24, the lubricious flushing liquid can flow from compartment 23 at a predetermined low pressure or flow rate, continuing to lubricate the prosthetic valve and the components of the catheter assembly 16. The flow of the flushing liquid may continue until deployment has been completed and the distal sheath 24 is again advanced into contact with atraumatic tip 14, closing compartment 23.

Although the disclosure herein has been described with reference to particular embodiments in which a prosthetic heart valve (e.g., aortic or mitral) is implanted into a patient, the disclosure contemplates applying the lubrication teachings herein to delivery devices configured to deliver any other catheter payload, such as any stent, valve, clip, or the like.

The disclosure herein has been described with reference to particular embodiments in which the catheter assembly is inserted into the patient through the femoral vein (i.e., transfemoral insertion), typically for accessing the mitral valve. However, it is to be understood that the disclosure contemplates embodiments in which the target site is accessed through other techniques. For example, to access the mitral valve, a surgical opening may be formed in the patient's chest and the catheter assembly may be inserted directly through the apex of the heart (i.e., transapical insertion) through a puncture in the right atrium and then transeptally into the left atrium, or directly through a puncture in the left atrium. The catheter assembly may also access the mitral valve through another portion of the vasculature of the patient. For example, the catheter assembly may be inserted through the jugular vein or through subclavian access into the superior vena cava, from there to the right atrium and then transeptally into the left atrium. Other percutaneous techniques may be used for accessing the aortic valve, tricuspid valve, pulmonic valve or any other structures in the interior of the heart or elsewhere in the patient's anatomy. In such embodiments, some of the delivery device components may have to be modified or may have to be oriented in a different direction to that described herein.

Although the disclosure herein has been described as including applying a lubricant such as albumin between an outer shaft 22 and an inner shaft 26 made of polymer materials such as polyimide, PEEK, or nylon, the lubrication teachings disclosed herein may be applied to coaxially aligned shafts of which one is made of a polymer and one is made of a metal, or of which both shafts are made of metal.

In summary, the disclosure herein describes multiple embodiments of a catheter assembly for delivering a medical implant that may include an inner shaft around which a compartment is defined, an outer shaft, a distal sheath, and a lubricant. The compartment may be adapted to receive the medical implant in an assembled condition. The inner shaft may have a radially outward-facing surface. The outer shaft may coaxially surround at least a portion of the inner shaft. The outer shaft may be movable in longitudinal directions relative to the inner shaft and may define a lumen therein having a radially inward-facing surface. The inner shaft and the outer shaft may together define a space between the outward-facing surface of the inner shaft and the inward-facing surface of the outer shaft. The space may provide liquid communication between a proximal end of the catheter assembly and the compartment. The distal sheath may be fixedly connected to the outer shaft. The distal sheath may be movable in the longitudinal directions between a closed condition covering the compartment and an open condition uncovering the compartment for deployment of the medical implant. The lubricant may contain albumin and may be disposed within at least a portion of the space; and/or the inner shaft and the outer shaft may each include respective polymers; and/or at least one of the inner shaft or the outer shaft may include a metal; and/or the catheter assembly may be coupled to an operating handle, and the operating handle may include a hemostasis valve in liquid communication with the space; and/or the catheter assembly may also include the medical implant disposed within the compartment; and/or the medical implant may be a prosthetic heart valve; and/or the catheter assembly may also include a recirculating pathway outside of the outer shaft providing liquid communication between the proximal end of the catheter assembly and the distal sheath.

Also described herein are multiple embodiments of a delivery device for a medical implant, the delivery device including an operating handle having a housing and a carriage movable in longitudinal directions relative to the housing, and a catheter assembly. The catheter assembly may include an inner shaft around which a compartment is defined, an outer shaft, a distal sheath, and a lubricant. The inner shaft may be operatively connected to the housing. The compartment may be adapted to receive the medical implant in an assembled condition. The inner shaft may have a radially outward-facing surface. The outer shaft may coaxially surround at least a portion of the inner shaft. The outer shaft may be fixedly connected to the carriage and may be movable in the longitudinal directions relative to the inner shaft and the housing. The outer shaft may define a lumen therein having a radially inward-facing surface. The inner shaft and the outer shaft may together define a space between the outward-facing surface of the inner shaft and the inward-facing surface of the outer shaft. The space may provide liquid communication between the operating handle and the compartment. The distal sheath may be fixedly connected to the outer shaft. The distal sheath may be movable in the longitudinal directions between a closed condition covering the compartment and an open condition uncovering the compartment for deployment of the medical implant. The lubricant may contain albumin and may be disposed within at least a portion of the space; and/or the inner shaft and the outer shaft may each include respective polymers; and/or at least one of the inner shaft or the outer shaft may include a metal; and/or the catheter assembly may be coupled to the operating handle, and the operating handle may include a hemostasis valve in liquid communication with the space; and/or the catheter assembly may also include the medical implant disposed within the compartment; and/or the medical implant may be a prosthetic heart valve; and/or the delivery device may also include a recirculating pathway outside of the outer shaft providing liquid communication between the operating handle and the distal sheath.

Further described herein are multiple embodiments of a method of lubricating a catheter assembly that is configured to deliver a medical implant. The method may include providing the catheter assembly, the catheter assembly including an inner shaft around which a compartment for the medical implant is defined, an outer shaft coaxially surrounding at least a portion of the inner shaft, a distal sheath fixedly connected to the outer shaft, the distal sheath being movable in longitudinal directions between a fully closed condition covering the compartment and an open condition uncovering the compartment, the inner shaft and the outer shaft together defining a space therebetween providing liquid communication between a proximal end of the catheter assembly and the compartment. The method may also include mounting the medical implant in the compartment, sliding the distal sheath to cover the compartment and the medical implant, and flushing a lubricant containing albumin through the space between the compartment and the proximal end of the catheter assembly; and/or the catheter assembly may be coupled to an operating handle having a hemostasis valve in liquid communication with the space, and the flushing step may include flushing the lubricant through the hemostasis valve; and/or the method may also include flowing the lubricant from the compartment to the proximal end of the catheter assembly and recirculating the lubricant out from the proximal end of the catheter assembly back into the compartment; and/or the method may also include, before the mounting step, inserting the medical implant into a bath of the lubricant containing albumin; and/or the method may also include inserting a distal end of the catheter assembly into a patient and deploying the medical implant by moving the distal sheath from the fully closed condition to the open condition; and/or the method may include flowing the lubricant through the compartment during the deploying step; and/or the medical implant may be a prosthetic heart valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of lubricating a catheter assembly that is configured to deliver a medical implant, the method comprising:
   providing the catheter assembly, the catheter assembly including an inner shaft around which a compartment for the medical implant is defined, an outer shaft coaxially surrounding at least a portion of the inner shaft, a distal sheath fixedly connected to the outer shaft, the distal sheath being movable in longitudinal directions between a fully closed condition covering the compartment and an open condition uncovering the compartment, the inner shaft and the outer shaft together defining a space therebetween providing liquid communication between a proximal end of the catheter assembly and the compartment;
   mounting the medical implant in the compartment;
   sliding the distal sheath to cover the compartment and the medical implant;
   inserting a distal end of the catheter assembly into a vasculature of the patient and deploying the medical implant by moving the distal sheath from the fully closed condition to the open condition;
   flushing a lubricant containing albumin through the space between the compartment and the proximal end of the catheter assembly;
   flowing the lubricant through the compartment during the deploying step;
   flowing the lubricant from the compartment to the proximal end of the catheter assembly; and
   recirculating the lubricant out from the proximal end of the catheter assembly back into the compartment.

2. The method of claim 1, wherein the catheter assembly is coupled to an operating handle having a hemostasis valve in liquid communication with the space, and the flushing step includes flushing the lubricant through the hemostasis valve.

3. The method of claim 1, further comprising, before the mounting step, inserting the medical implant into a bath of the lubricant containing albumin.

4. The method of claim 1, wherein the medical implant is a self-expanding prosthetic heart valve.

5. The method of claim 4, wherein deploying the medical implant includes allowing the self-expanding prosthetic heart valve to self-expand into a native heart valve annulus.

6. The method of claim 5, further comprising:
   after deploying the self-expanding prosthetic heart valve, resheathing the self-expanding prosthetic heart valve into the compartment.

7. The method of claim 5, wherein flowing the lubricant through the compartment during the deploying step reduces a force required to retract the distal sheath off of the medical implant, thereby reducing a force required for deployment.

* * * * *